(12) United States Patent
Santos (10) Patent No.: US 8,442,775 B2
(45) Date of Patent: May 14, 2013

(54) SYSTEM AND METHOD FOR MONITORING DISSOLVED GASES IN INSULATING OIL OF HIGH VOLTAGE EQUIPMENT

(76) Inventor: Eduardo Pedrosa Santos, Atibaia (BR)

( * ) Notice: Subject to any disclaimer, the term of this patent is extended or adjusted under 35 U.S.C. 154(b) by 264 days.

(21) Appl. No.: 12/753,252

(22) Filed: Apr. 2, 2010

(65) Prior Publication Data

US 2011/0246088 A1  Oct. 6, 2011

(51) Int. Cl.
*G01N 33/28* (2006.01)
*G06F 19/00* (2011.01)

(52) U.S. Cl.
USPC ........... 702/24; 73/19.01; 73/19.02; 702/182; 702/188

(58) Field of Classification Search .......... 702/24, 702/31, 32, 33, 85, 105, 182, 183, 188; 73/19.01, 73/19.02, 25.01; 96/6
See application file for complete search history.

(56) References Cited

U.S. PATENT DOCUMENTS

| | | | |
|---|---|---|---|
| 4,236,404 A * | 12/1980 | Ketchum et al. | 73/19.02 |
| 5,400,641 A * | 3/1995 | Slemon et al. | 73/19.01 |
| 5,773,709 A | 6/1998 | Gibeault et al. | |
| 6,391,096 B1 | 5/2002 | Waters et al. | |
| 7,647,202 B2 * | 1/2010 | Lamontagne | 702/182 |
| 7,747,417 B2 * | 6/2010 | Lamontagne | 702/188 |

OTHER PUBLICATIONS

Serveron, "On-Line Transformer Monitor Installation Guide", Model TM Series, 810-1644-01 Rev C, Mar. 28, 2008 (copyright 2008), retrieved on Mar. 31, 2010 and available online using Internet http://www.bplglobal.net/eng/knowledge-center/download.aspx?id=270.
GE Energy Management, HYDRAN(R) 201R Model i, "On-Line Monitoring of Transformer Key-Fault Gases", retrieved on Mar. 31, 2010 and available online using Internet http://www.ge.com/de/downloads/Hydran_201R_Model_i_English.pdf.
GE Power Systems, "HYDRAN(R) M2 Fault Gas and Moisture Monitor, Substation Automation Solutions", retrieved on Mar. 31, 2010 and available online using Internet http://www.gepower.com/prod_serv/products/substation_md/en/downloads_en/hydra_nm2_fact_sheet.pdf.

* cited by examiner

*Primary Examiner* — John H Le
(74) *Attorney, Agent, or Firm* — McKee, Voorhees & Sease, P.L.C.

(57) ABSTRACT

A system and method for monitoring dissolved uses in insulating oil of power transformers and other high voltage equipment includes an orifice for accessing the insulating oil, and using a monitoring system to sample the oil and measure the concentration of different gases dissolved in the oil to determine what is going on inside the high voltage equipment.

16 Claims, 7 Drawing Sheets

SYSTEM AND METHOD FOR MONITORING DISSOLVED GASES IN INSULATING OIL OF HIGH VOLTAGE EQUIPMENT

FIELD OF THE INVENTION

This system and method aims at continuously and in real time monitoring the concentration of dissolved gases in the insulating oil of high voltage equipment, such as power transformers, reactors, condensive bushings, current transformers, potential transformers and others, in order to quickly detect faults occurrence when they are still in an incipient stage, thus avoiding catastrophic failures, frequently followed by explosion and fire, which may cause risks to the operation and maintenance personnel and may lead to the whole loss of the involved high voltage equipment.

BACKGROUND OF THE INVENTION

Power transformers, reactors, condensive bushings as well as other high voltage equipment are largely used in electric power generation, transmission and distribution systems, where they perform several essential roles, such a way that the continuity of the power supplying depend, for the most part, upon the reliability of such equipment.

The aforementioned high voltage equipment frequently use, as an insulating and heat removing mean, some type of either oil or insulating liquid, that may be mineral oil (petrol derived), vegetable oil (obtained from soy bean, from sunflower or from other source) or silicon, among others, henceforth simply referred either as "insulating oil" or "oil". All active parts of the equipment—core, windings, insulations, etc.—are immersed in insulating oil, in order to impregnate the paper and to assure the electric insulation of the assembly, besides providing the cooling of the active parts by means of such oil circulation in heat radiators.

Therefore, any inside fault occasionally occurred in an equipment, such as overheating points, bad contacts, partial discharges, arcs and others may provoke either oil or paper molecule breakage, generating gases that will dissolve into the oil. Types and volume of generated gases depend upon the kind of fault, upon its severity, upon the energy it may liberate as well as upon the materials involved in such fault (oil, paper, cupper, etc.).

Therefore, the measurement of those gases dissolved into the equipment may be used as a tool for a diagnosis of such equipment's status, allowing estimating existence (or not) of occasional defects, their nature and their intensity. With such measurements in hands, several techniques may be used for such data analyzing as well as for obtaining a diagnosis on the equipment status—transformer, reactor, etc. For clarification purposes, methodologies of the international standard IEC 60599—*Mineral oil-impregnated electrical equipment in service—Guide to the interpretation of dissolved and free gases analysis* as well as the Duval technique may be mentioned among others.

Such measurement has been traditionally made, at least since the 60's decade, by means of a laboratory analysis of an oil sample taken from the equipment, from which the dissolved gases are extracted and gas-chromatographically analyzed. More recently, starting from the 80's decade, the first on-line gas monitors appeared, which are permanently installed at the high voltage equipment where they continuously measure dissolved gases in real time.

Due to the importance of high voltage equipment for the reliability of the electric power generation, transmission and distribution, the on-line monitoring of gases dissolved in insulating oil has become an each time more common practice for the diagnosis as well as the prognosis in real time of the status of the equipment, for it allows detecting and diagnosing occasional faults with greater efficiency and quickness than samples laboratory analysis, avoiding therefore interruptions in power supplying, or, in other words, avoiding black-outs.

State of the Art

Devices and systems used in the state of the art for the on-line measurement of gases dissolved in insulating oil of high voltage equipment, such as power transformers for instance, may be split into two main categories: a) devices based on extraction and return of oil samples from and to the transformer tank by external tubing and b) devices that make contact with the insulating oil by means of one only great diameter valve at the transformer tank, as ahead described.

One of the devices used in the state of the art for the on-line measurement of gases dissolved in the insulating oil of high voltage equipment, such as high voltage transformer, and that fits into the first mentioned category, may be seen in U.S. Pat. No. 6,391,096, incorporated by reference herein, commercially used in the "On-line Transformer Monitor TM Series" product, of Serveron Corporation. As illustrated in the mentioned product documentation, Reference No. [1], incorporated by reference herein (see full citation at Table 1 infra), its operation is based upon the circulation in its inside of a sampling of the transformer's oil, which is done by means of an inlet tubing that connects to a valve on the transformer's tank wall and bears the oil to inside the equipment, where the gas is extracted from the oil and sent to a gases concentration measurement system, afterwards returning the oil to the transformer through an outlet tubing that connects to a second valve on the transformer's tank wall.

A pump inside the monitoring equipment forces the oil extracted from one of the transformer's tank valves to circulate, passing through the dissolved gases measurement system until its returning to the second tank valve, in order to obtain oil sampling which content of dissolved gases is well representative of the phenomena that occur inside the transformer. However, this is obtained by increasing oil leakage risks along the closed circuit where such oil circulates, due to the great number of elements as well as of sealed connections needed, which encloses two valves on the transformer tank wall, the tubing connections to these two valves as well as the connections of both same tubing to the measurement equipment, besides the connections inside the measurement equipment. Besides the greater number of connections and sealing elements needed, such arrangement contributes to a larger risk of leakages also due to the several meters length of mentioned tubing, that are, therefore, exposed to a greater risk of accidental damages during the transformer's maintenance works, where going up and down of maintenance personnel on its lateral walls as well as same personnel walking on its upper cover accomplishing various tasks in such places, usually using heavy tools, is very common.

Another feature of the mentioned state of the art is the need of using two gas cylinders near to the in oil dissolved gases measurement equipment, with the purpose of carrier gas for the gas-chromatographycal process of measurement as well as of checking gas for such same process calibrating. The existence of such two cylinders brings the need of their periodic replacement, for their contents are gradually consumed during the measurement system operation. Therefore, a new item requiring preventive maintenance—replacement of empty gas cylinders by full ones—is incorporated to the dissolved gases monitoring system, which originally has as one of its purposes that of altering the maintenance philosophy of the transformer from preventive (based on the operation time) to predictive (based on the equipment status). When taking into consideration that one only electric power concessionary may have either hundreds or even thousands of transformers in its installed base, besides other high voltage equipment immersed in oil, the simple periodic replacement of cylinders may undertake a great extent, with the need of creating specific professional teams to take care of the gases in real time monitoring equipment, which consequently provokes an increase in maintenance costs as well as a deviation of the maintenance engineering focusing which should always be fully directed to the transformer.

In the second category of monitoring equipment for the real time monitoring of gases dissolved in oil, devices may be found that make contact with the insulating oil by a sole valve of great diameter in the transformer tank, such as "Hydran 201R Model i" and "Hydran M2" products, respectively shown in Reference Nos. [2] and [3], incorporated by reference herein (see full citations at Table 1, infra). Due to the fact that the oil flow from the transformer tank to inside the measurement equipment is made by one only valve, such systems require the valve as well as the piping used for such connection to have a relatively large diameter, even larger than a certain minimum specified diameter, and the length for the oil running from the transformer tank to inside the equipment to be the shortest possible, shorter than certain maximum length specified by its manufacturer. Therefore, the aim is to avoid the oil inside the measurement equipment to stand stagnated, where its dissolved gases content may not be representative anymore of the transformer internal condition.

In order to force the oil circulation between the equipment inner part and the transformer, a mean shown in U.S. Pat. No. 5,773,709 (incorporated by reference herein), is also used where the oil inside the equipment is cyclically heated and cooled in order to constrain its circulation by the convection phenomenon. However, the required use of relatively large diameter valves makes, in several facilities of transformers already in operation, the tank empting or draining valve to be the only available option, for it is the sole large diameter valve present. However, the draining valve location at the lowest tank point, at a level below the active part, where the heat that provokes the oil circulation inside the transformer is generated, may lead the oil to therein stagnate, and the circulation caused by the heating of the measurement equipment to merely be local, and, therefore, poorly representing the dissolved gases in the remainder portion of the transformer. Besides, sometimes the draining valve is already used in other tasks, such as the oil circulation either in oil thermo-vacuum regeneration machines or others, which obliges to remove and to reinstall the measurement equipment each time the valve's use is needed.

In current state of the art of dissolved gases monitoring equipment, semi-permeable membranes are frequently used in the extraction of the gas dissolved in oil. Such membranes have such a porosity that, despite allowing one or more gases to move across them, they prevent the oil from passing through. Therefore, a construction is used where the insulating oil is placed at one side of the membrane and a gaseous environment is placed at the other side, where the gases extracted from the oil will be measured. As the membrane side in gaseous environment usually is at, or near to, atmospheric pressure, the membrane is submitted to and must support the pressure difference between the oil and the atmosphere. In the majority of the applications, and in normal operational conditions, the oil pressure should be equal to the atmospheric pressure plus the hydrostatic pressure of the oil column, usually of some meters. In such case, the pressure difference that must be supported by the membrane is merely the pressure corresponding to the oil column height, which is relatively low. Situations may arise, however, where such pressure difference significantly increases, which may damage the membrane and cause an oil leakage through it, which puts the state of the art monitoring equipment out of order and causes oil pouring in the environment. Examples of situations that may cause such damages to the membrane are the vacuum creation inside the transformer tank during tests or oil treatment processes, and an excessive pressure or vacuum occurring, respectively, during the installation or the removal of the valve of the transformer of the monitoring equipment without opening the air purging orifice to allow a pressure balancing between the valve inside and the environment.

State of the Art Disadvantages

In the case of systems with piping circulation systems, the high leakage risks along the oil closed circulation system, due to great number of elements and connections needed as well as to the great tubing length, that are exposed to accidental damages;

In the case of systems with connection to one only valve, the requirement of using a relatively large diameter valve which will increase installation costs of new transformers;

Due yet to the requirement of using large diameter valve, the obligation of a connection to the draining valve of the transformer in many installations performed in transformer already in operation, obliging to the removal of the monitoring system each time the valve must be used in another application;

In a case of installation at the draining valve, the risk for the dissolved gases measurement to be done in stagnated oil, poorly representative of the phenomena that occur in the transformer, which will lead to a low quality diagnosis;

The use, in some monitoring systems, of gas cylinders that must be periodically replaced, incorporating a new item that will require a periodic preventive maintenance, when the purpose of monitoring is the periodic maintenance to be eliminated. As an electric power utility may possess hundreds or thousands of transformers, there will be hundreds or thousands of cylinders to maintain, which also contributes to deviate the focus of the maintenance professionals from their main tasks;

The risk of damages to the monitoring equipment semi-permeable membrane in case of overpressure or vacuum that may occur either when installing and removing the system or when the transformer would be submitted to maintenance and tests;

The risks of environment contaminating in case of insulating oil leakage, due to the aforementioned factors;

Due to the high costs associated to the state of the art monitoring systems, the economic infeasibility of their use in small size transformer and other equipment used at the thousands in electric power distribution systems, leaving those equipment deprived of on-line monitoring and subject to catastrophic failures.

BRIEF SUMMARY OF THE INVENTION

Invention Object

The invention aims to continuously and in real time monitoring the concentration of gases in the insulating oil in high voltage equipment, such as, for instance, power transformers, reactors, condensive bushings, current and potential transformers among others, made by means of an orifice of reduced diameter, with no need of any tubing along the transformer, which will assure the access to a sample of oil which will the best representative of what may be going on inside the high voltage equipment.

Invention Advantages

Leakage risk reduction by eliminating oil circulating tubing;
Possibility of using small diameters valves or orifices for the installation of the gases monitoring system, thus reducing costs and avoiding to occupy the draining valve, at the same time allowing its installation in good oil circulation parts, such as heat radiators;
Possibility of deepness adjusting of the oil collection orifices, precisely placing them at places where oil would be best representative of what is going on inside the high voltage equipment;
Calibrating gas cylinders elimination, by use of a self calibration system using environmental air, therefore assuring measurements precision and avoiding the need of periodic gas cylinders maintenance;
Elimination of semi-permeable membrane damage risk due to overpressure or vacuum in the oil during the installation or the maintenance of the transformer;
Reduction of environmental risks by oil contamination in case of leakages, as stated in above items;
Quick connection system by inlet and removable plug, reducing installation and maintenance times;
The possibility of simplified versions construction, of low cost, with sensors for just some gases measuring, such as one, two, three gases and so on;
The possibility of very low cost versions building, only acting as a "gas switch" for alarm, allowing monitoring of small size transformers and other equipment used at the thousands in power distribution.

DETAILED DESCRIPTION OF THE PREFERRED EMBODIMENTS

The new invention herein described deals with a "SYSTEM AND METHOD FOR MONITORING DISSOLVED GASES IN INSULATING OIL OF POWER TRANSFORMERS, REACTORS, ON-LOAD TAP CHANGERS, CURRENT TRANSFORMERS, POTENTIAL TRANSFORMERS, CONDENSIVE BUSHINGS AS WELL AS SIMILAR HIGH VOLTAGE EQUIPMENT IMMERSED IN OIL", mainly consisting of a system that is coupled to one only orifice for the insulating oil accessing, being such orifice of small diameter and avoiding the use of tubing along the transformer, which allows its installation, for instance, at the orifices present in air purging radiators, thus assuring to the monitoring system the access to an oil sampling that will represent in an excellent manner what is going on inside the high voltage equipment. Besides allowing a simple and safe installation in the high voltage equipment, such system also has the self-calibration recourse as well as several possible user's interfaces, as well analogical as digital.

Figure 1:
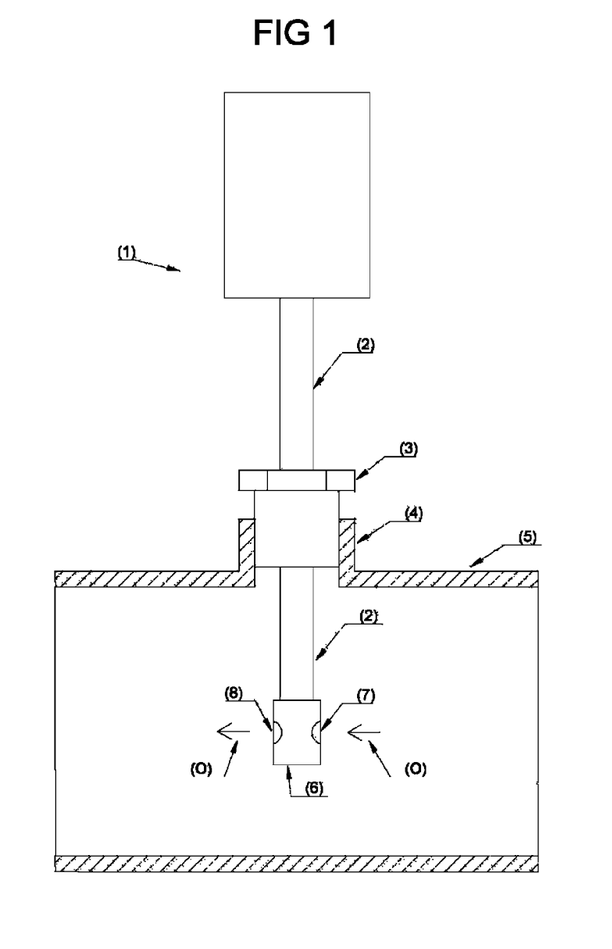
FIG. 1: Interface of the gases in oil monitoring system with high voltage equipment.

More particularly, referring to FIG. 1, the gases monitoring system (1) herein described is compound by a rigid cylindrical rod (2), endowed with a anchorage device (3) for its fixation to an orifice (4) that allows access to the oil (O) of the high voltage equipment (5), so that the lower end (6) of the rod (2) may be inserted through the orifice (4) until reaching a place where oil (O) circulation already naturally exists, having such rod end (6) two openings (7, 8) diametrically opposed, one for oil inlet (7) and the other for oil discharge (8).

Figure 2:
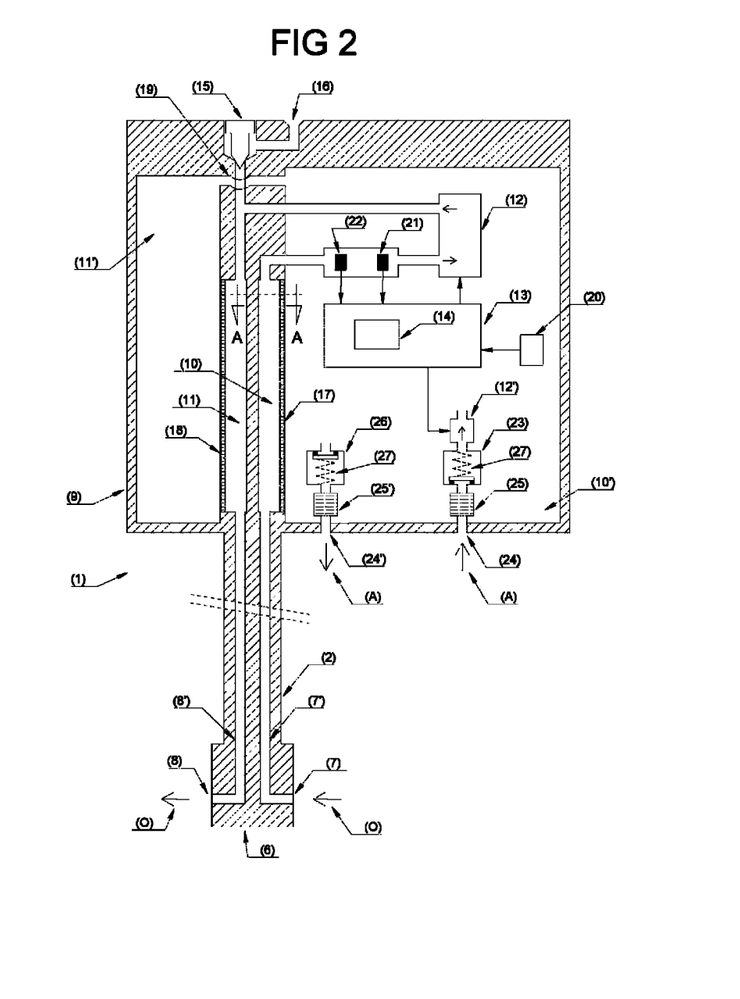
FIG. 2: Details of the gases in oil monitoring system.

As FIG. 2 shows, where the gases monitoring system may be seen in crossed section, each one of the openings (7, 8) is connected to a tubing (7', 8') for oil circulation, being such tubing (7', 8') axially placed inside the rod (2) and both parallel to each other. The upper end of the rod (2) is fixed to a main body (9), in which inside there are two oil chambers (10, 11), each one connected to one of the oil circulation tubing (7', 8'). Both oil chambers (10, 11), on their turn, are interconnected in their upper portion by means of an oil circulation pump (12). Such oil pump (12) is controlled by a microprocessor (13), that switches it on or off in accordance with a program in its software (14). When the oil pump (12) is in operation, it forces the oil (O) to circulate, by entering through the inlet orifice (7), travelling through the inlet tubing (7'), entering into the first oil chamber (10), passing through the pump (12), entering into the second oil chamber (11), passing through the outlet tubing (8') and finally returning to the high voltage equipment (not shown) after having left the discharge orifice (8).

Observing a little more the FIG. 2, the upper part of the main body (9) is endowed with a small air purging valve (15), that keeps contact with the upper part of the oil chamber (11) as well as with the oil outlet of the pump (12), in order to allow the elimination, or purge, of the air present inside the oil chambers (10, 11) and tubing (7', 8') at the very moment of the installation, this way assuring its full filling with oil. When opening the purge valve (15) the oil raises inside the chambers (10, 11) and tubing (7', 8'), expelling the air through the nozzle (16). Such arrangement may be also used for the collection of oil samples for laboratorial analysis, by coupling a sampling syringe (not shown) to the nozzle (16), for the oil expelled through the nozzle to fill the syringe when the valve (15) would be opened.

According to FIG. 2, each one of the oil chambers (10, 11) has one or more walls constituted by membranes (17, 18) of a semi-permeable material, that allows the gas dissolved in oil (O) to permeate to the gas chambers (10', 11'), which are interconnected by channel (19). In the gas chamber (10') one or more sensors (20) are installed to measure the concentration of the gas object of interest for monitoring, as, for instance, hydrogen, carbon monoxide, carbon dioxide, methane, ethane, ethylene and acetylene, among others. As the gas chambers (10', 11') are hermetically sealed, the gases concentration in its inside is directly proportional to the in oil (O) dissolved gases, so that the measurement made by the sensors (20) may be used by the micro-processor (13) to calculate those gases concentration in the oil (O).

As the forced circulation of oil (O), in contact with the membranes (17, 18), by means of the oil pump (12), very much increases the efficiency of the gases permeation through the membranes, there will be no need for a continuous operation of the oil pump (12) for an enough volume of in oil (O) dissolved gases be obtained in the gas chambers (10', 11') to allow sensors (20) to read their concentrations. This way, it becomes possible to increase the useful life of the oil pump (12) by operating it in an intermittent and cyclic manner, switching it on for a certain period of time and switching it off for a second period of time. This is done by the software (14) processed by the micro-processor (13), where such periods of time are previously programmed in order to assure a volume of in oil (O) dissolved gases sufficient to allow its measurement to permeate through the membranes (17, 18).

Still considering FIG. 2, a humidity sensor (21) is installed in the oil (O) circulation track, to measure the relative saturation of water dissolved in oil (O), and to inform such measurement to the micro-processor (13). At the same place, a temperature sensor (22) is installed, which will supply the micro-processor (13) with oil (O) temperature information. The micro-processor (13), after receiving the water relative saturation as well as oil temperature measurements, shall proceed in its software (14) to calculate the water concentration in oil (O) in parts per million. Such measurements also allow the micro-processor (13) to make calculations in its software (14) aiming to compensate and to correct any occasional influences that the variations of the water saturation as well as of the oil (O) temperature saturation may provoke in the gases sensors (20) measurements, allowing therefore precise measurement of gases in any temperature and humidity conditions.

Referring to FIG. 2, in cases where gases sensors (20) require oxygen for their proper operation, the presence of such element in the gas chambers (10', 11') is assured by the air pump (12'), which draws oxygen from the atmospheric air (A). The air pump (12') is controlled by the micro-processor (13), that switches it on and off according to the program in its software (14). When the air pump (12') would be operating, the vacuum generated at its inlet will force the inlet check valve (23) to open, therefore creating an air flow (A) that passes through the air inlet orifice (24), through the filter (25) for particles as well as humidity retention, through the inlet check valve (23) and through the air pump (12'), afterwards entering into the gas chamber (10'). Such air flow (A), when entering into the gas chamber (10'), creates a positive pressure therein, which leads the exhaust check valve (26) to open, allowing the air (A) to outgo through the air filter (25') as well as allowing the air exhaust orifice (24') to open, in order to avoid an excessive pressure inside the gas chamber and allowing the air renewal in its inside, which assures an oxygen concentration constantly equal to that found in the atmosphere. In order to avoid the gases intended to be measured to be fully expelled from the gas chamber (10'), the air pump (12') operates in an intermittent and cyclic way, as programmed in the software (14) processed by the micro-processor (13), for the air pump switching on during a certain period of time and switching off during a second period of time. Such time periods are previously programmed in the micro-processor (13) control software in order the air pump (12') to stay switched off during the greatest length of the time—situation where the inlet (23) and exhaust (26) retention valves are closed by their internal springs (27), maintaining both gas chambers (10', 11') hermetically sealed and therefore avoiding the gases that permeated the membranes (17, 18) to disperse into the atmosphere as well as allowing their concentrations in the gas chambers (10', 11') to balance with the concentration of same in oil (O) dissolved gases—and switched on during short periods to assure the oxygen supply to the inside of the gas chamber (10', 11').

On the other hand, the air pump (12') also allows a self-calibration process of the gas monitoring system (1). For such purpose the air pump (12') is switched on for a period of time long enough for the whole volume of gas inside the gas chambers (10', 11') to be expelled and substituted by atmospheric air (A), where the concentrations of the gases measured by the sensors (20) are known, allowing the control software (14) in the micro-processor (13) to compare the sensors (20) measurements to the known concentrations values, calculating measurements errors and discounting these from those, such a way that the measurements shall be corrected and shall match the known values of gases concentration in atmosphere. Due to the fact that during the described self-calibration process the in oil (O) dissolved gases measurements are interrupted, this procedure must be performed at relatively large intervals, as for instance, once a day or once a week, for the software (14) processed in the micro-processor (13) allows the user to program the periodicity of the self-calibration.

Figure 3:
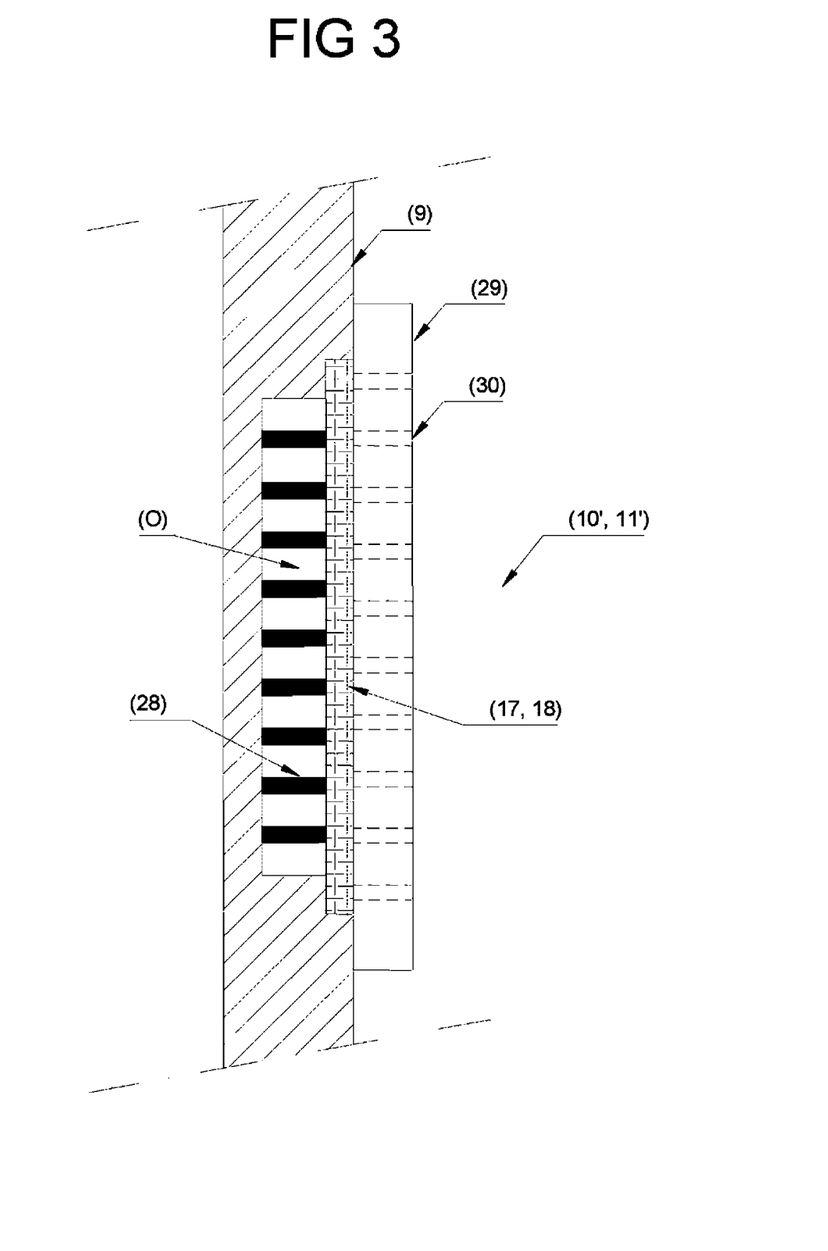
FIG. 3: Details of the semi-permeable membrane.

As detailed in FIG. 3, where the cross section A-A appointed in FIG. 2 is shown, semi-permeable membranes (17, 18) have, on their side in contact with the oil (O), a set of support fins (28) that touch the membrane (17, 18), such fins (28) spaced one from another in order to allow the oil (O) to pass through the spaces amid them. In the case of vacuum occurring in the oil (O), such fins (28) act as supports for the membranes (17, 18), supporting them in order to avoid them to stretch and to be submitted to excessive forces, which may lead to their rupture, provoking an oil (O) leakage. Similarly, on the membranes (17, 18) opposite side, aside the gas chambers (10', 11'), there are support plates (29) fixed to the main body (9), having such support plates (29) a large number of holes (30), that allow the gas permeated through the membranes (17, 18) to reach the gas chambers (10', 11'). In the case of an overpressure occurring in the oil (O), such support plates (29) will act as supports for the membranes (17, 18), supporting them in order to avoid them to stretch and to be submitted to excessive forces that may cause oil (O) leakage in the same manner.

Figure 4:
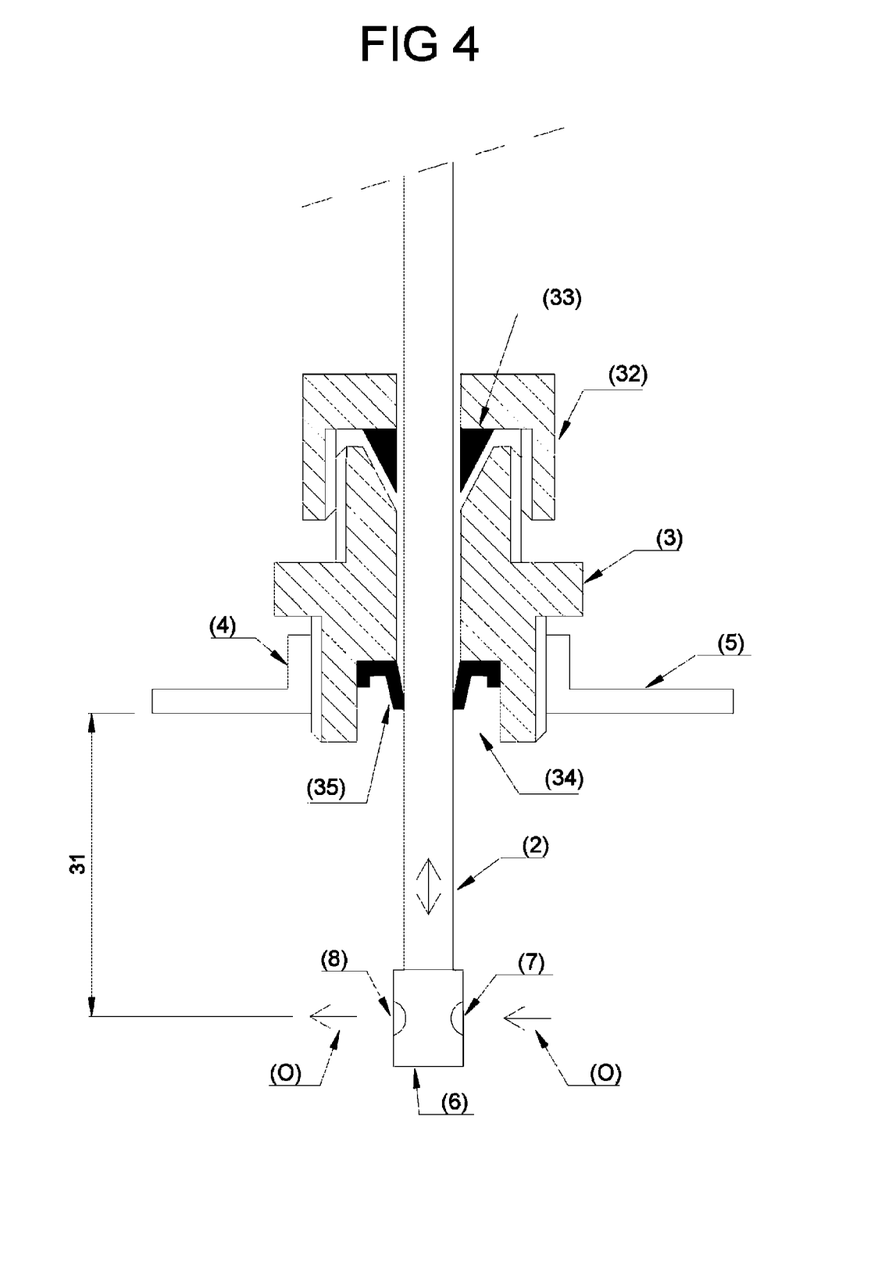
FIG. 4: Details of anchorage device.

FIG. 4 shows a cross section of the anchorage device (3), with the rod (2) in its inside. In such figure, it may be observed that to assure the oil (O) inlet orifice (7) as well as the oil (O) outlet orifice (8) at the end (6) of the rod (2) to be properly placed in an area where circulation of high voltage equipment oil does exist, the anchorage device (3) has a cylindrical hole at its center that allows the rod (2) to freely move in its own axial direction, all along its length, therefore varying the deepness (31) where the inlet (7) and outlet (8) orifices are placed referred to opening (4) of the equipment tank (5), where the anchorage device (3) is bolted. After the deepness (31) having been adjusted, the rod (2) is firmly held by fastening the nut (32), which pushes down the ring (33), wedge shaped and made of either metallic or elastic material, such a way that it will radially press as well the rod (2) as the anchorage device (3), impeding the rod (2) to move inside the anchorage device (3) and therefore avoiding deepness (31) accidentally to alter. For more safety, the lower end (6) of the rod (2) has a diameter larger than the rest of the rod (2) as well as larger than central hole of the anchorage device (3), therefore impeding the rod (2) to separate from the anchorage device (3), this way avoiding oil (O) to leak, as, for instance, in case of oil (O) overpressure. To avoid oil (O) leakage through the small space between the rod (2) and the central hole of the anchorage device (3), this has a cavity (34) in its lower part where a lip seal (35) is installed, that maintains a radial pressure on the rod (2), avoiding oil (O) to pass, despite allowing axial movement of the rod (2).

As it may be observed in FIGS. 1, 2 and 4, the oil sampling manner used by the gas monitoring system (1) herein described allows to use one only orifice (4) for its connection to the high voltage equipment (5)—being possible the orifice (4) to be endowed with a full opening type valve, usually spherical or gate valve—also allowing this to have a diameter reduced as much as desired, being ½ inch the typically used diameter.

Figure 5:
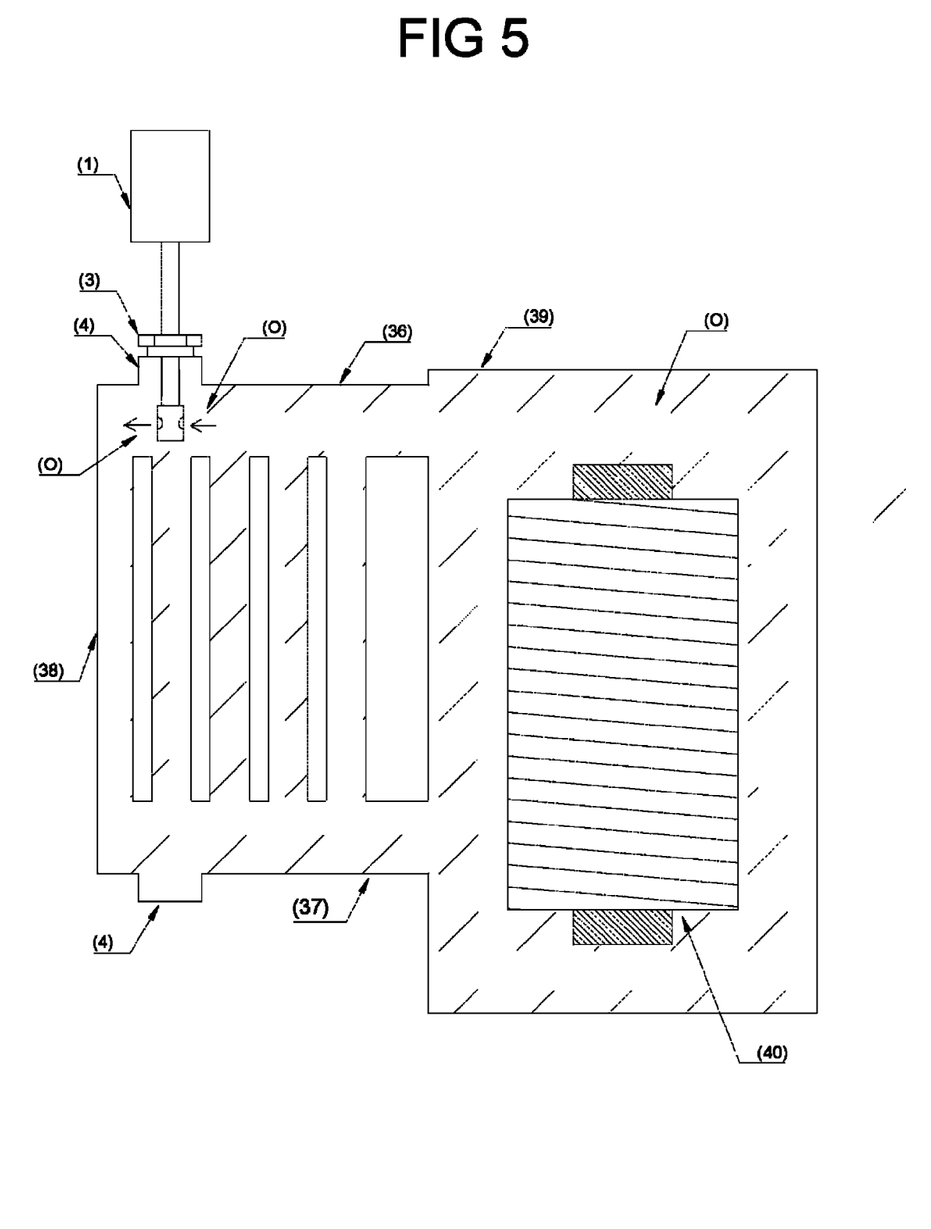
FIG. 5: Installation at heat radiators tubing.

As FIG. 5 shows, the small needed diameter for the orifice (4) allows the gases monitoring system (1) to be installed either in the upper tubing (36) or in the lower ones (37) of the heat radiators (38) of a power transformer or of a reactor (39), at the orifices (4) of a small diameter, present in the upper tubing (36) for the air removing from inside the radiators (38) during the oil (O) filling operation of the transformer and in the lower tubing (37) for same radiator (38) empting for maintenance purposes. Therefore, the gases monitoring system (1) collects its sample in an oil flow (O) fully representative of the inside transformer (39) status, for such oil flow directly proceeds from the active part (40) of the equipment (39), being this flow provoked by the heat in this same active part (40)—core and windings—by convection effect, which makes the hot oil (O) entering through the upper tubing (36), passing through the radiators (38) and returning cooled to the transformer (39) through the lower tubing (37), being yet possible the use of, in some applications, pumps (not shown) for a forced oil circulation through the radiators (38), creating an even greater flow. Despite the FIG. 5 illustrates the gases monitor (1) in the orifice (4) of the upper tubing (36), it is also possible to install the gases monitor (1) in the orifice (4) of the lower tubing (37).

Therefore, referring to FIGS. 2 and 5, the oil circulation tubing (7', 8') are of a quite reduced length, due to the fact that the main body (9) of the gases monitoring system (1) is directly fixed to the rod (2) end, avoiding such tubing (7', 8') to extend along the walls and/or along the transformer cover (39), where they may be damaged during maintenance operations, besides being them protected in the rod (2) inside.

Figure 6:
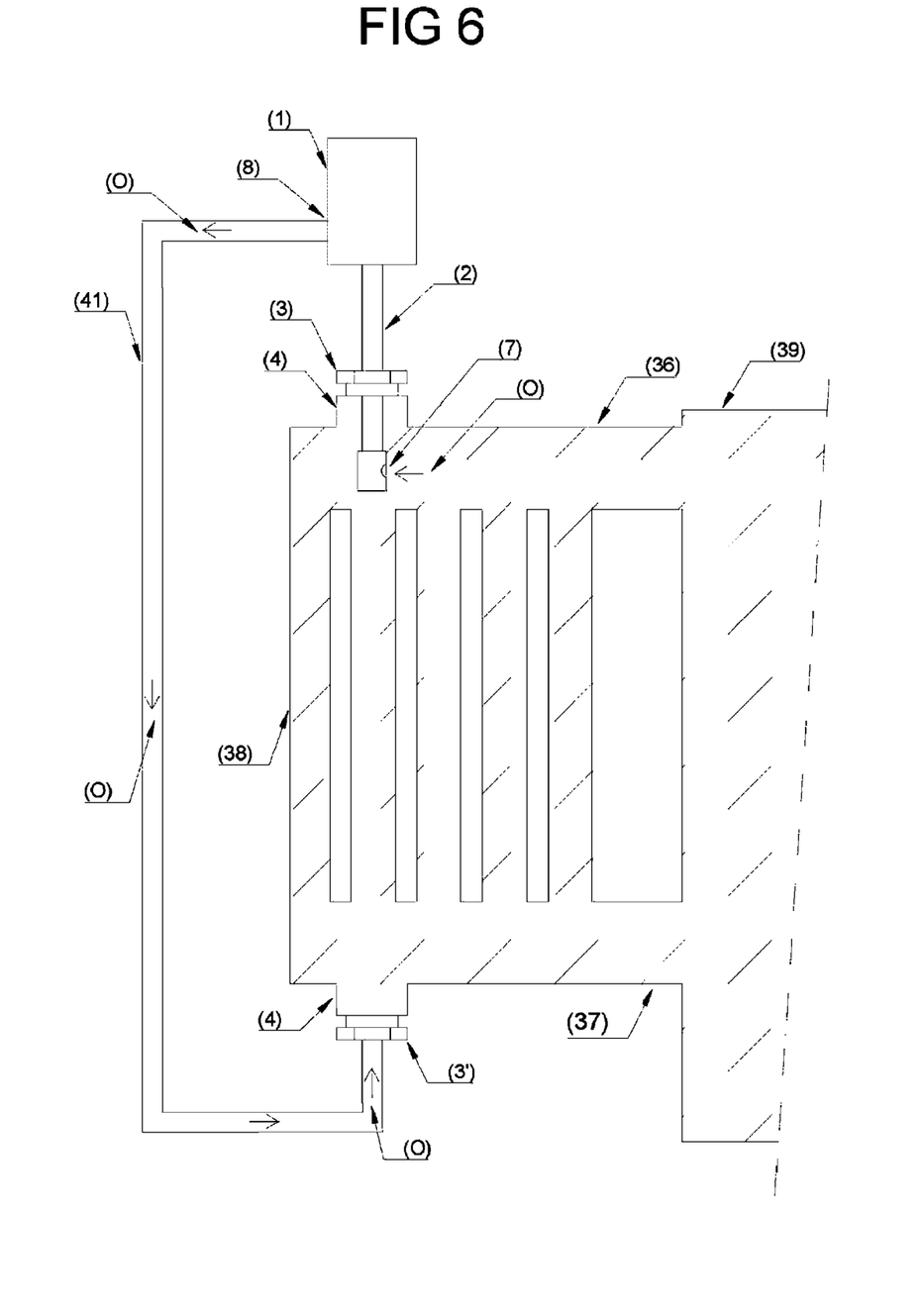
FIG. 6: Alternative installation at heat radiators tubing.

However, such fact does not impede the use of the gases monitoring system (1) with other configurations, one of them shown in FIG. 6, where it may be observed that the oil (O) admission occurs through the inlet orifice (7) present at the lower end of the rod (2) and the oil exit occurs through the discharge orifice (8), that connects by means of the outside tubing (41) and of the anchorage device (3') to the orifice (4) present at the lower tubing (37) of the radiators (38). Other installation arrangements of the gases monitoring system (1) are also possible, and it may be mentioned, with no intention of all possibilities exhausting, the gases monitoring system (1) to be installed at the orifice (4) of the lower tubing (37) and the tubing (41) to be connected, by means of the anchorage device (3'), to the orifice (4) of the upper tubing (36), taking notice that, in such case, the end of the rod (2) will possess a discharge orifice (8) and the tubing (41) will connect to the gases monitor (1) at its inlet orifice (7).

Figure 7:
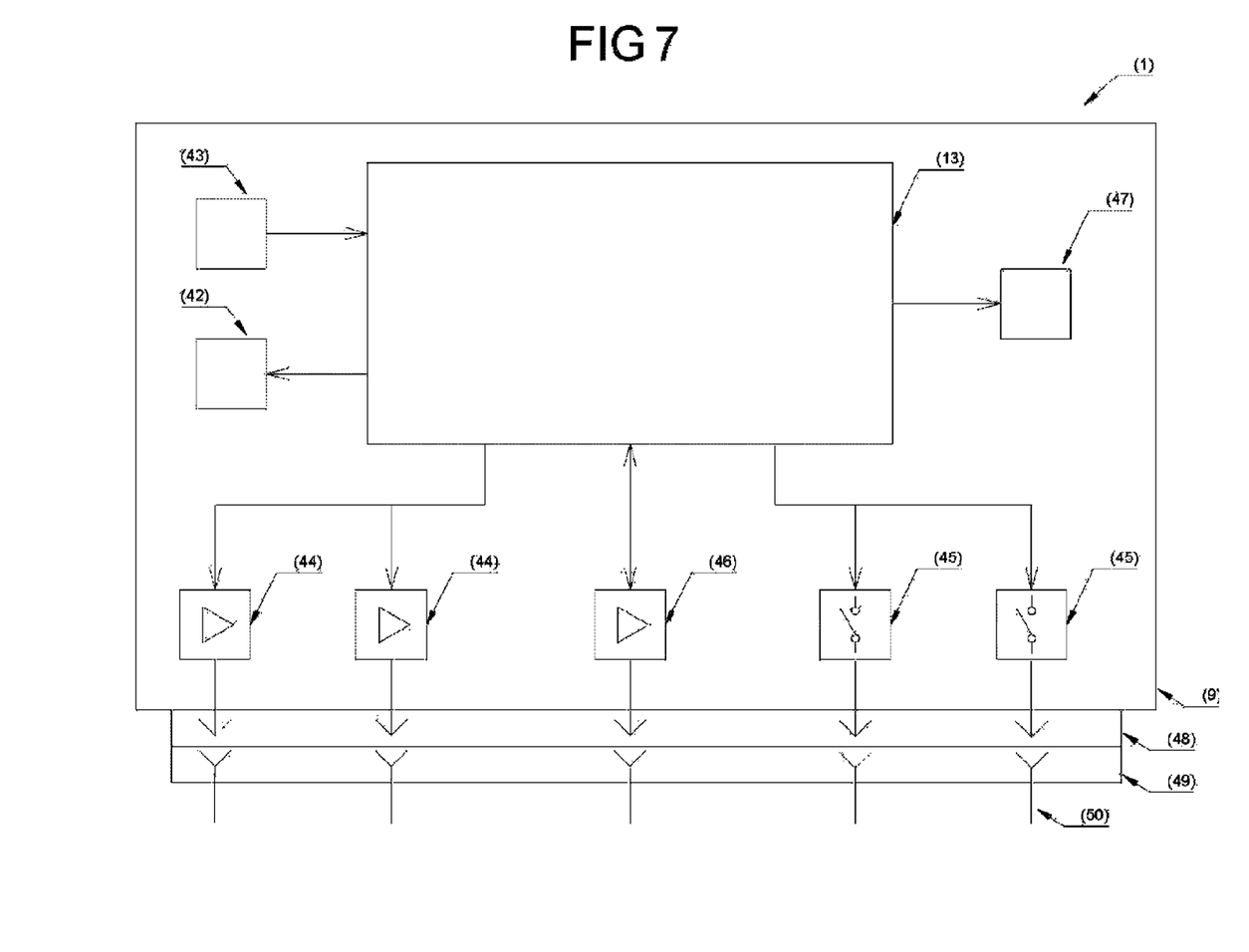
FIG. 7: Block diagram of the circuits.

As block diagram of FIG. 7 shows, the in oil dissolved gases monitoring system (1) is equipped with a display (42), connected to the micro-processor (13), for the local appointing of the in oil dissolved gases concentration values, oil temperature, relative saturation of water in oil and water dissolved in oil concentration, among others, and with a keyboard (43) for local adjustments by the user. For remote appointment of these same information, the system (1) has two analogical outputs (44), of type 4-20 mA for instance, which are controlled by the micro-processor (13), that also operates output relays (45) for several alarms appointing, such as either high or very high gases concentrations, water saturation in oil either high or very high as well as high rates of increase of gases concentration as well as of water content in oil. There are also serial communication ports (46) associated to the micro-processor (13), RS232, RS485, USB types or others, for instance, that allow remote reading of all measurement, by means of a remote computer of data acquisition (not shown), besides circuits (47) for remote transmission of measurement by means of radio waves, in Wi-fi, Zigbee, Bluetooth or others standards, just to mention possible examples. For installation and removal easiness, all electric connections required for the operation of the gases monitoring system (1) are made by means of an outlet (48) permanently fixed to the main body (9), to which a removable plug (49) is connected, to which the user will connect all required wiring (50), there enclosing auxiliary feeding voltage for the system, analogical output signals as well as alarm relays and serial communication ports, among others.

Gases monitoring system (1) may also be built in simplified versions of lower cost, with one only gas sensor (20) installation, for only hydrogen concentration measuring, for instance, or with two gas sensors (20), for two gases concentration measuring—for instance, hydrogen and carbon monoxide, not excluding other combinations—and so on, with sensors for three gases, four gases etc. . . .

Besides, the gases monitoring system (1) may also be built in an extremely low cost configuration, where it will act as a "gas switch", i.e., an equipment endowed with one or more sensors (20) that have the purpose of only detecting great extent increases occurrence in the concentration of selected gases—for instance, gas concentration reaching twice or thrice its initial value, not minding in doing any precise measurement of such concentrations. When such abrupt concentrations increases occur, the gases monitoring system (1) activates one or more output contacts (45), informing the user about such happening, for him to take the required measures, such as oil samples collecting for laboratorial analysis for a precise diagnosis of the fault in the high voltage equipment. Unlikely the complete hardware configuration shown in FIG. 7 and above described, parts considered as non essential may be eliminated in this very low cost version, such as the local display (42), the keyboard (43), the analogical outlet (44), the serial communication ports (46) as well as the wi-fi communication circuits (47), only remaining the alarm outlet contacts (45). Such configuration of very low cost brings as a benefit the fact that it allows the on-line monitoring of small size and low cost transformers and other high voltage equipment, used at the thousands in electric power distribution systems, where high cost complete gases monitoring systems installation is economically unviable.

TABLE 1

[1] SERVERON, "On-Line Transformer Monitor Installation Guide", Model TM Series, 810-1644-01 Rev C, Mar. 28, 2008 (copyright 2008), retrieved on Mar. 31. 2010 and available online using Internet http://www.bplglobal.net/eng/knowledge-center/download.aspx?id=270
[2] GE Energy Management, HYDRAN ® 201R Model i, "On-Line Monitoring of Transformer Key-Fault Gases", retrieved on Mar. 31. 2010 and available online using Internet http://www.ge.com/de/downloads/Hydran_201R_Model_i_English.pdf
[3] GE Power Systems, "HYDRAN ® M2 Fault Gas and Moisture Monitor, Substation Automation Solutions", retrieved on Mar. 31. 2010 and available online using Internet http://www.gepower.com/prod_serv/products/substation_md/en/downloads_en/hydranm2_fact_sheet.pdf

What is claimed is:

1. A system for monitoring dissolved gases in high voltage equipment immersed in insulating oil, the system comprising:

a cylindrical rigid rod (2), endowed with an anchorage device (3) for its fixing to an orifice (4) which gives access to oil (O) of the high voltage equipment (5);

for a lower end (6) of the rod (2) inserted through the orifice (4) until it reaches a place where there is a natural oil circulation (O);

two orifices (7, 8) diametrically opposed at the lower end (6) of the rod (2), one for oil inlet (7) and the other for oil outlet (8);

tubing (7', 8') of oil circulation connected to these orifices (7,8), that are axially placed inside the rod (2) and parallel to each other;

the upper end of the rod (2) to he rigidly fixed to a main body (9), inside of which there are two oil chambers (10, 11), each one connecting to the tubing (7', 8'), both oil chambers (10, 11) being interconnected at their upper parts by means of a pump (12) of oil circulation, which is controlled by the micro-processor (13), which switches it on and off according to a program present in its software (14);

wherein the oil pump (12), when in operation causes oil (O) circulation, which enters through the inlet orifice (7), moves through the inlet tubing (7'), enters into the first oil chamber (10), passes through the pump (12), enters into the second oil chamber (11), passes through outlet tubing (8') and returns to the high voltage equipment (5) after having left the discharge orifice (8);

wherein each of the oil chambers (10, 11) have one or more of their walls constituted by membranes (17, 18) made of semi-permeable material, that allow dissolved gas in oil (O) to permeated into gas chambers (10', 11'), that are interconnected by channel (19);

at least one sensor (20) by the gas chamber (10') for measurement of a concentration of concerned gases intended to be monitored, gas chambers (10', 11') being hermetically sealed, making gases concentration in its inside directly proportional to the concentration of dissolved gases in the oil (O), such that concentration measurements made by the sensors (20) may be used by the micro-processor (13) for calculations in its software (14) of the same gases in oil (O) concentration;

an air pump (12'), that, by means of the inlet (23) and exhaust (26) check valves obtains oxygen from the atmospheric air (A) to assure oxygen presence in the gas chambers (10', 11'), the air pump (12') being controlled by the micro-processor (13), that switches the air pump (12') on and off in an intermittent and cyclic manner, according to a program present in the software (14) processed by the micro-processor (13).

2. The system according to claim 1, wherein it allows the oil pump (12) to operate in an intermittent and cyclic manner to increase its life, switching it on for a certain period of time and switching it off for second period of time, as programmed in the software (14) processed by the micro-processor (13), in order to assure a volume of in of (O) dissolved gases to permeate through the membranes enough to allow their concentrations to be read by sensors (20).

3. The system according to claim 1, wherein the inlet cheek valve (23) is forced to open by the vacuum generated at the inlet of the air pump)(12') when it is in operation, provoking an air flow (A) that passes through the air admission orifice (24), through the filter (25) for humidity and particles retaining, through the admission retention valve (23) and through the air pump (12'), entering into the gas chamber (10'), where a positive pressure is generated that leads to the exhaust check valve (26) to open, allowing the outgoing of the air (A) through the filter (25') as well as through the air exhaust orifice (24'), in order to avoid an excessive pressure inside the gas chamber (10') and to allow the air renewal in its inside, assuring therefore a constant concentration of oxygen equal to that found in the atmosphere: by the air pump (12') operation to be made in an intermittent and cyclic manner, as programmed in the software (14) processed by the microprocessor (13), in order to switch the air pump on for a certain period of time and switch it off for a second period of time, being such periods of time previously programmed in the control software of the micro-processor (13) in order to the air pump (12') to stay switched off for the greatest part of the time, being only switched on for short periods of time to assure the oxygen supply inside the gas chambers (10', 11'); by the inside springs (27) to close the admission (23) as well as the exhaust (26) check valves when the air pump (12') is switched off, keeping the gas chambers (10', 11') hermetically sealed and avoiding therefore the dispersion into the atmosphere of the gases that permeated thorough the membranes (17, 18) and making possible their concentrations in the gas chambers (10', 11') to balance with the concentration of the same gases dissolved in oil (O).

4. The system according to claims 1 or 3, wherein the air pump (12') allows the process of a self-calibration of the gas monitoring system (1), that consists in switching the air pump (12') on for a certain period of time long enough for all the gas inside the gas chambers (10', 11') to be expelled and replaced by atmospheric air (A), where the concentrations of the gases measured by the sensors (20) is known, allowing the control software (14) in the micro-processor (13) to compare the measurements of the sensors (20) against the known concentrations values, to calculate the errors of the measurements and to discount those from these, in order to the measurements to be corrected and to come to match the known concentrations of such gases in the atmosphere, being the performing periodicity of the self-calibration procedure controlled by the software (14), processes in the micro-processor (13), in accordance with a configuration made by the user.

5. The system according to claim 1, wherein the upper part of the main body (9) has an air purging valve (1 5), that keeps contact with the upper part of the of chamber (11) as well as with the oil pump (12) outlet, in order to allow the elimination, or purge, of the air present at the inside of the oil chambers (10, 11) as well as of tubing (7', 8') when opening the purge valve (15), being the air expelled by the nozzle (16) by allowing the collecting of samples of oil for laboratorial analysis, by coupling a sampling syringe to the nozzle (16), in order the oil expelled through the nozzle (16) to fill the syringe when opening the valve (15).

6. The system according to claim 1, wherein a humidity (21) sensor for the relative saturation of water dissolved in oil (O) measuring and an oil temperature sensor (22) are installed in the oil (O) circulation track, for them to supply to the micro-processor (13) the information of their measurements, wherewith the micro-processor (13) may process in its software (14) the calculation of the water in oil (O) concentration, in parts per million, as well as the calculations for compensating and correcting occasional influences that the water saturation and oil (O) temperature may provoke in the gases sensors (20) measurements.

7. The system according to claim 1, wherein it has a set of support fins (28) aside the semi-permeable membranes (17, 18) which is in contact with the oil (O), such fins touching the membranes (17, 18) to avoid damaging the semi-permeable membranes (17, 18) in case of a vacuum in oil (O) and being such fins (28) spaced one from another in order to allow the oil (O) to flow amid them.

8. The system according to claim 1 or 7, wherein it has support plates (29) fixed to the main body (9), in contact with membranes (17, 18) aside the gas chambers (10', 11') to avoid damaging the membranes (17, 18) in case of overpressure in Oil (O), being such support plates (29) endowed with a great number of holes (30), that allow the gases permeated through the membranes to reach the gas chambers (10', 11').

9. The system according to claim No. 1, wherein the anchorage device (3) has a cylindrical hole at its center that allows the rod (2) to freely move in its axial direction, all along its length, therefore varying the deepness (31) where the admission (7) and exhaust (8) orifices are placed in connection with the orifice (4) of the equipment tank (5), where the anchorage device (3) is bolted, in order to assure the oil admission (7) and the oil (O) exhaust (8) orifices at the end (6) of the rod (2) to be properly located in an area where high voltage equipment oil circulation will be present; by the rod (2) to be held fastening the nut (32), that pushes down the ring (33), wedge shaped and made of either metallic or elastic material, for the latter to radially press as well the rod (2) as the anchorage device (3), impeding the rod (2) to move inside the anchorage device (3) and therefore avoiding the deepness (31) accidentally to alter; by the lower end (6) of the rod (2) to have a diameter larger than the rest of the rod (2) and larger than the central hole diameter in the anchorage device (3), in order to impede the rod (2) to separate from the anchorage device (3), avoiding therefore an of (O) leakage by the anchorage device central hole (3) to have a cavity (34) in it lower part where a lip seal (35) is installed, that keeps a radial pressure on the rod (2), avoiding therefore an oil (O) leakage through the small space between the rod (2) and the central hole of the anchorage device (3), despite allowing the axial movement of the rod (2).

10. The system according to claim 1 or 9, wherein it allows the use of one only orifice (4) for the gas monitoring system (1) connecting to the high voltage equipment (5), also allowing the orifice (4) to have a diameter reduced as much as desired, making possible the gas monitoring system (1) to be installed either in the upper tubing (36) or in the lower tubing (37) of the heat radiators (38) of either a power transformer or reactor (39), in the small diameters orifices (4) present in the upper tubing (36), to the air removal from inside the radiators (38) during the filling operation of the transformer with the oil (O), as well as in the lower tubing (37) for the same transformers (38) empting for maintenance purposes.

11. The system according to claim 1 or 9, wherein the oil circulation tubing (7', 8') has a length quite reduced, due to the fact that the main body (9) of the gases monitoring system (1) is directly fixed to the end of the rod (2), therefore avoiding such tubing (7', 8') to extend along the transformer's walls and/or the transformer's cover (39), where they could be damaged during maintenance works, besides being them protected inside the rod (2).

12. The system according to claim 1 or 9, wherein it allows, in an alternative arrangement, the oil (O) admission occurs through the admission orifice (7) in the lower end (6) of the rod (2), installed at the orifice (4) of the upper tubing (36), and the oil exhaust to occur through the discharge orifice (8), that connects by means of the external tubing (41) as well as of the anchorage device (3') to the orifice (4) present at the lower tubing (37) of the radiators (38), also allowing the gases monitor installation (1) at the orifice (4) of the lower tubing (37) as well as the connection of the tubing (41), by means of the anchorage device (3'), to the orifice (4) of the upper tubing (36), being that in such case the end of the rod (2) will have a discharge orifice (8) and the tubing (41) will connect to the gases monitor (1) at its admission orifice (7).

13. The system according to claim 1, wherein the oil dissolved gases monitoring system (1) is equipped with a display (42), connected to the micro-processor (13), for the local appointing of the concentration values of the dissolved gases in oil, of the oil temperature, of the relative water saturation in the oil as well as of the concentration of water dissolved in oil, among others, and with a keyboard (43) for local adjustments by the user; by the gases monitoring system (1) to be endowed with analog outputs (44), controlled by the micro-processor (13), that also operates output relays (45) for several alarms appointing; by having serial communication ports (46), associated to the micro-processor (13), that allow the remote reading of all measurements, by means of a remote computer of data acquisition, besides circuits (47) for the remote measurements transmitting by means of radio waves; by all electric connections required for the gases monitoring system (1) operation to be made by means of an outlet (48) permanently fixed to the main body (9), to which a removable plug (49) is connected, to which the user may connect all required wiring (50).

14. The system according to claim 1 or 13, wherein the gases monitoring system (1) may be built in simplified versions of lower cost, for only some gases measuring, by installing only some sensors (20)—one, two, three sensors and so on.

15. The system according to claim 1 or 13, wherein the gases monitoring system (1) may be built in a very low cost configuration, where it will act as a "gas switch", equipped with one or more low cost sensors (20) that have the purpose of only detecting the occurrence of great extension increases in concentrations of selected gases, doing no precise measurement at all of such concentration, actuating one or more output contacts (45) when occurring such abrupt increase in concentrations to impart the occurrence to the user.

16. The system according to claim 1 or 13, wherein a very low cost version of the gases monitoring system (1) allows non essential parts to be eliminated, such as the local display (42), the keyboard (43), the analog outputs (44), the serial communication ports (46) as well as the wireless communication circuits (47), only remaining the output contacts for alarm.

* * * * *

UNITED STATES PATENT AND TRADEMARK OFFICE
CERTIFICATE OF CORRECTION

PATENT NO.          : 8,442,775 B2                                        Page 1 of 1
APPLICATION NO.     : 12/753252
DATED               : May 14, 2013
INVENTOR(S)         : Eduardo Pedrosa Santos It is certified that error appears in the above-identified patent and that said Letters Patent is hereby corrected as shown below:

In the Claims:

Col. 11, Claim 3, line 58:
DELETE after inlet "cheek"
ADD after inlet --check--

Col. 12, Claim 5, Line 41:
DELETE after of the "of"
ADD after of the --oil--

Col. 13, Claim 8, Line 5:
DELETE "Oil"
ADD --oil--

Col. 13, Claim 9, Line 27:
DELETE after an "of"
ADD after an --oil--

Col. 13, Claim 10, Line 41:
BEFORE reactor ADD --a--

Signed and Sealed this
Eighteenth Day of June, 2013

Teresa Stanek Rea
*Acting Director of the United States Patent and Trademark Office*